United States Patent
Hsieh et al.

(10) Patent No.: US 7,772,015 B2
(45) Date of Patent: Aug. 10, 2010

(54) OBSERVATION METHOD OF WAFER ION IMPLANTATION DEFECT

(75) Inventors: Yi-Wei Hsieh, Taipei County (TW); Jeremy Duncan Russell, Taoyuan County (TW); Pei-Yi Chen, Taoyuan County (TW)

(73) Assignee: Inotera Memories, Inc., Taoyuan County (TW)

( * ) Notice: Subject to any disclaimer, the term of this patent is extended or adjusted under 35 U.S.C. 154(b) by 100 days.

(21) Appl. No.: 12/258,694

(22) Filed: Oct. 27, 2008

(65) Prior Publication Data

US 2010/0015735 A1 Jan. 21, 2010

(30) Foreign Application Priority Data

Jul. 18, 2008 (TW) .............................. 97127302 A (51) Int. Cl.
*H01L 21/66* (2006.01)

(52) U.S. Cl. .................. 438/10; 438/17; 257/E21.527; 257/E21.53; 257/E21.531

(58) Field of Classification Search .................. 438/10, 438/11, 17, 18, FOR. 142; 257/48, E21.527, 257/E21.53, E23.531
See application file for complete search history.

(56) References Cited

U.S. PATENT DOCUMENTS

| | | | | |
|---|---|---|---|---|
| 5,200,112 A | * | 4/1993 | Angelopoulos et al. | 252/500 |
| 5,256,877 A | * | 10/1993 | Czernuszka et al. | 850/9 |
| 5,406,116 A | * | 4/1995 | Wills et al. | 257/630 |
| 5,783,366 A | * | 7/1998 | Chen et al. | 430/311 |
| 6,368,940 B1 | * | 4/2002 | Amon et al. | 438/424 |
| 6,808,948 B1 | * | 10/2004 | Tu et al. | 438/17 |
| 6,858,450 B1 | * | 2/2005 | Doan et al. | 438/14 |
| 6,933,158 B1 | * | 8/2005 | Lensing et al. | 438/16 |
| 7,063,991 B1 | * | 6/2006 | Zhao et al. | 438/14 |
| 7,112,288 B2 | * | 9/2006 | Clark et al. | 216/59 |
| 7,183,183 B2 | * | 2/2007 | Duerksen et al. | 438/524 |
| 7,635,920 B2 | * | 12/2009 | Travis et al. | 257/797 |
| 7,679,083 B2 | * | 3/2010 | Sun et al. | 257/48 |
| 2007/0251551 A1 | * | 11/2007 | Korzenski et al. | 134/41 |
| 2008/0092949 A1 | * | 4/2008 | Cheung et al. | 136/255 |
| 2008/0138972 A1 | * | 6/2008 | Kang et al. | 438/595 |
| 2008/0182422 A1 | * | 7/2008 | Edelberg et al. | 438/725 |
| 2008/0265251 A1 | * | 10/2008 | Xiao et al. | 257/48 |

* cited by examiner

*Primary Examiner*—George Fourson
(74) *Attorney, Agent, or Firm*—Rosenberg, Klein & Lee (57) ABSTRACT

An analysis method of wafer ion implant is presented, the steps of the method comprises: (a) cleave a wafer for analysis, and (b) from these pieces of wafers determine which ones are wafer with defect and set an insulator on the wafer with defect, (c) finally, use scanning electron microscope to observe whether the ion implant on the wafer with defect was correct or not. Whereby, engineers can take less time to analyze whether the ion implant of the wafer is correct or not with 100% repeatability.

14 Claims, 9 Drawing Sheets

OBSERVATION METHOD OF WAFER ION IMPLANTATION DEFECT

BACKGROUND OF THE INVENTION

1. Field of the Invention

The present invention relates to methods of wafer feature observation; in particular, to observation methods of wafer ion implantation defect.

2. Description of Related Art

In wafer fabrication, ion implantation is an essential process for changing the physical properties, and through an acceleration process, ion acquires the necessary energy to be injected into wafers and stay at a certain depth from the surface of the wafers. Since ion implantation is one of the critical factors affecting the quality of the wafer, engineers perform ion implantation analyses on flawed/defected wafers to understand whether the causes for such flaws are related with ion implantation failure, many techniques are developed for detecting implant levels, like SIMS (secondary ion mass spectrometry) and SCM (scanning capacitance microscopy), but necessary capital expenditure of these equipments are high. Another approach to visualize dopant regions is to use standard SEM (Scanning electron microscope) equipment junction staining. Before performing the analyses, it is necessary to prepare samples to be analyzed. First, engineers cleave a wafer for analysis, and perform a polishing action on these pieces of wafer with flaws. Next, immerse the sample in chemical solution in several seconds for decoration. Since the ion implantation states for P-type regions and N-type regions of the wafer are different, etching topography for P-type regions and N-type regions by the chemical decoration vary as well, such that the surface of the wafer presents a non-flat state. Finally, using scanning electron microscope to observe whether the ion implantation is successful; if the ion implantation is proven to have failed, the root cause have to be found and solved.

However, chemical decoration quite inefficient regarding the time spent on the steps of polishing and chemical decoration, which usually takes nearly one hour; and variations that may negatively affecting etching by the chemical decoration are many, for example poor control over immersion duration, or changes of properties/natures in the chemical decoration itself and the like; hence, successful operations are not easy, thereby causing low repeatability in such analysis results. Apart from this, a new method of ion implantation visualization referred as dopant contrast has been developed; however, so far its effect of use is not satisfactory due to low level of contrast.

Accordingly, the inventors of the present invention, having considered the above-mentioned improvable defects, devoting long-term efforts in researches together with field applications of theoretical knowledge, proposed the present invention with reasonable design and effective improvements over the disadvantages illustrated supra.

SUMMARY OF THE INVENTION

In view of the aforementioned issues, one essential objective of the present invention is to provide an observation method of wafer ion implantation defect which can largely reduce the time required for an entire analysis flow and provide 100% of repeatability on analysis results.

To achieve the above-stated objective, the present invention provides an observation method of wafer ion implantation defect, comprising the following steps: cleaving a wafer for analysis and setting an insulator on the surface thereof; using a scanning electron microscope to observe whether the ion implantation of the wafer with defect is successful.

The present invention provides another observation method of wafer ion implantation defect, comprising the following steps: sampling a wafer; cleaving the wafer for analysis; selecting a piece of wafer with defect as a sample; setting an insulating tape on the surface thereof, and placing the sample installed with the insulating tape under a scanning electron microscope to observe the state of the ion implantation on the wafer with defect.

The present invention provides the following benefits: since the placement of insulator on the surface of a piece of wafer with defect is relatively easier, as compared with chemical decoration which requires in-situ experiences of engineers for each successful operation, thereby improving possibility of successful operation and accordingly offering 100% of repeatability for analysis results. On the other hand, since the preparation of wafer samples does not require processes of polishing and chemical decoration, time spent on entire analysis workflow can be thus significantly reduced.

DETAILED DESCRIPTION OF PREFERRED EMBODIMENTS

Figure 1:
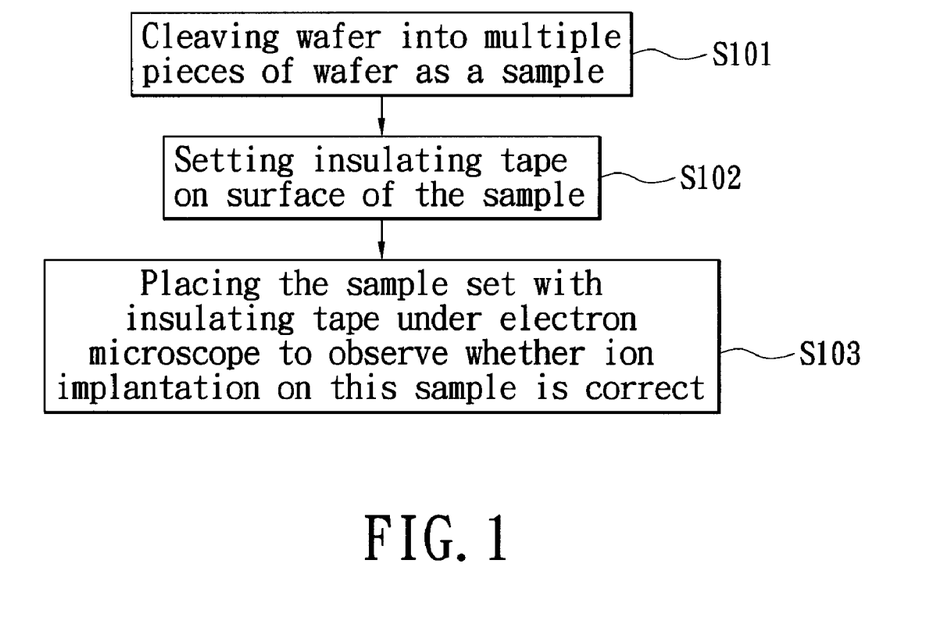
FIG. 1 is a flowchart of a first embodiment for the observation method of wafer ion implantation flaw/defect according to the present invention.

As shown in FIG. 1, the present invention provides a first embodiment for an observation method of wafer ion implantation defect, comprising the following steps:

S101: initially, cleaving a wafer along the direction of crystal orientation into multiple pieces of wafer;

S102: next, among these pieces of wafer, selecting the pieces of wafer with defect as a sample, and setting by attachment an insulating tape on the surface of the sample; in this way, preparations of samples for ion implantation analysis are accomplished; and S103: finally, using a scanning electron microscope to observe whether the ion implantation on the sample is successful. Acceleration voltage range of the scanning electron microscope is set to be within 1000 volts~3000 volts, working distance range is between 1.5 mm~8 mm; operational parameters may vary depending on the scanning electron microscopes of different venders, for clear observation of ion implantation distribution.

Figure 2:
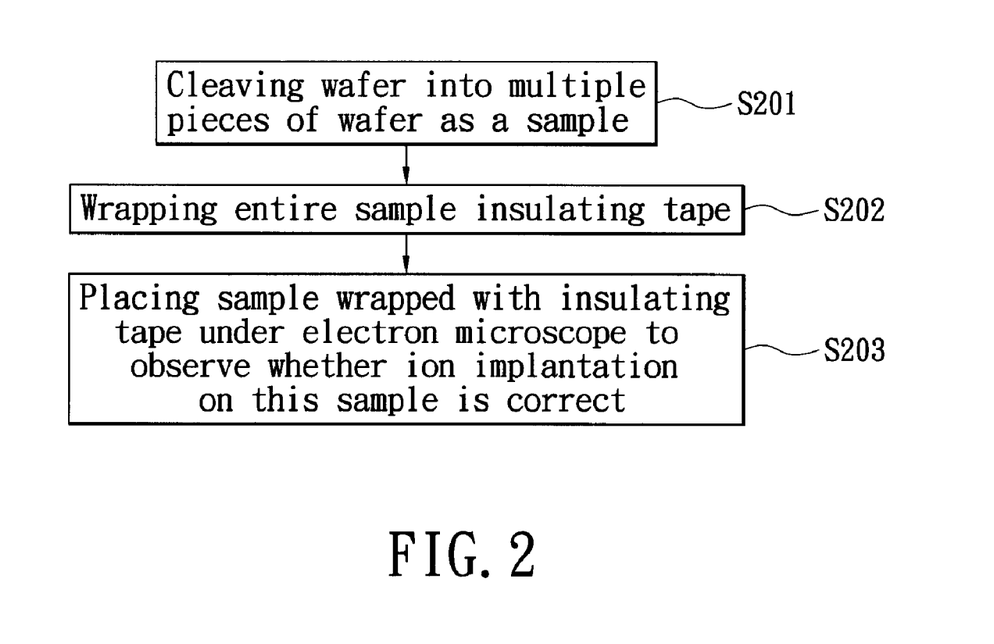
FIG. 2 is a flowchart of a second embodiment for the observation method of wafer ion implantation flaw/defect according to the present invention.
Figure 3:
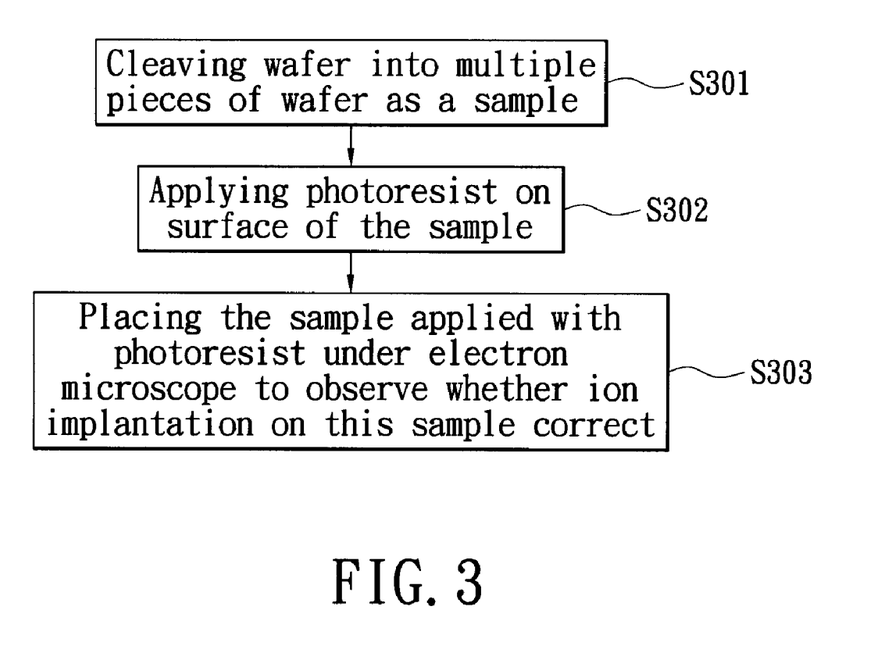
FIG. 3 is a flowchart of a third embodiment for the observation method of wafer ion implantation flaw/defect according to the present invention.
Figure 4:
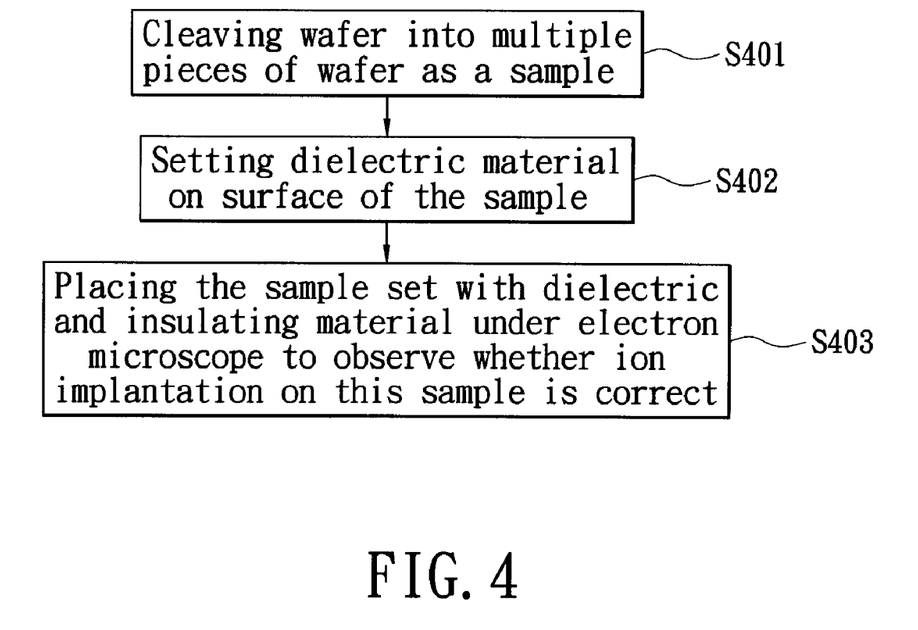
FIG. 4 is a flowchart of a fourth embodiment for the observation method of wafer ion implantation flaw/defect according to the present invention.
Figure 5:
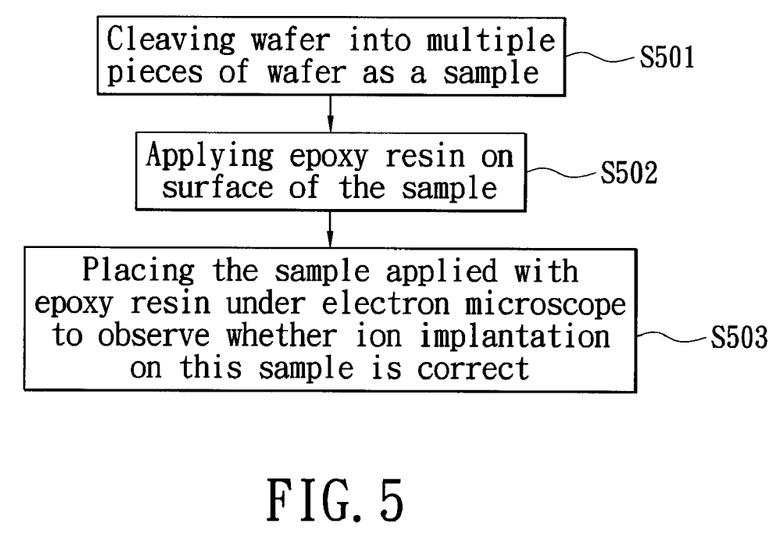
FIG. 5 is a flowchart of a fifth embodiment for the observation method of wafer ion implantation flaw/defect according to the present invention.

In the above-said step S102, there exist other options in types of insulators and different operations thereof, hereunder are a few embodiments listed for reference:

(a) as shown in FIG. 2 (second embodiment: S201~S203), wrapping entire sample with an insulating tape (S202);

(b) as shown in FIG. 3 (third embodiment: S301~S303), applying a insulator, and the insulator is a photoresist, wherein the photoresist is dispersed on the surface of the sample (S302);

(c) as shown in FIG. 4 (fourth embodiment: S401~S403), applying a layer which is dielectric and insulating material, wherein the dielectric and insulating material is placed on the surface of the piece of wafer with defect (S402), and can optionally consist of silicon dioxide, silicon nitride, or silane nitride, etc.;

(d) as shown in FIG. 5 (fifth embodiment: S501~S503), applying an insulator, and the insulator is an epoxy resin, wherein the epoxy resin is placed on the sample (S502).

Figure 6:
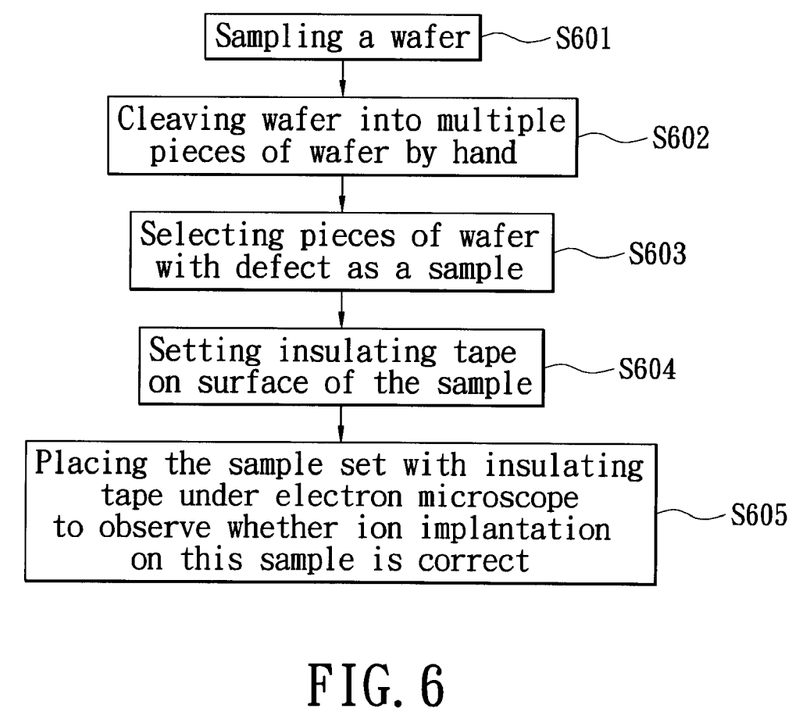
FIG. 6 is a flowchart of a sixth embodiment for the observation method of wafer ion implantation flaw/defect according to the present invention.

As shown in FIG. 6, the present invention provides a sixth embodiment for an observation method of wafer ion implantation defect, comprising the following steps:

S601: sampling a wafer;

S602: cleaving the wafer into multiple pieces of wafer by hand;

S603: selecting pieces of wafer with defect as a sample;

S604: applying insulating tapes on the sample; and

S605: placing the sample under a scanning electron microscope to observe the ion implantation distribution.

Figure 7:
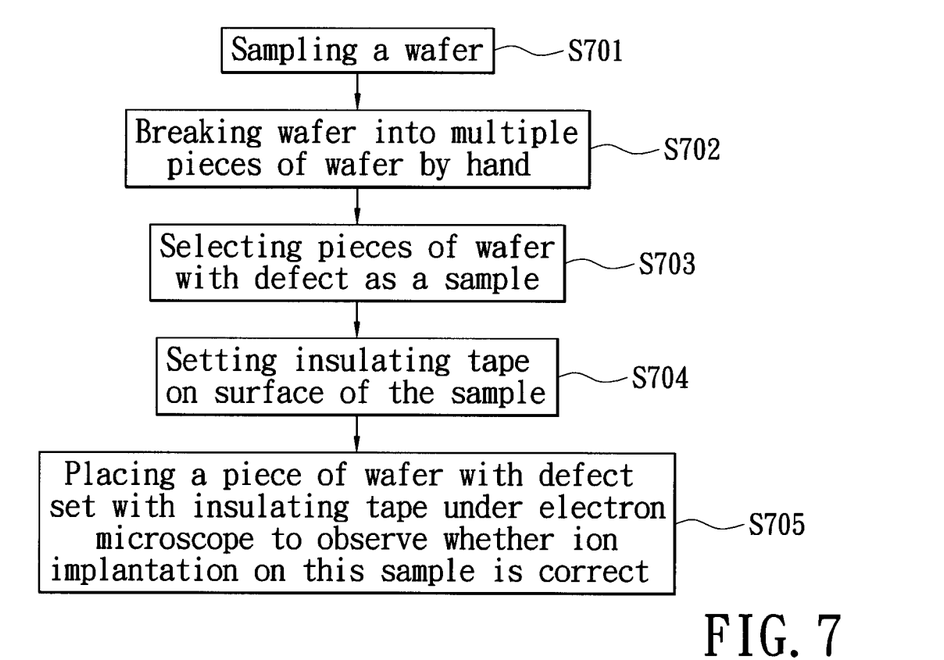
FIG. 7 is a flowchart of a seventh embodiment for the observation method of wafer ion implantation flaw/defect according to the present invention.
Figure 8:
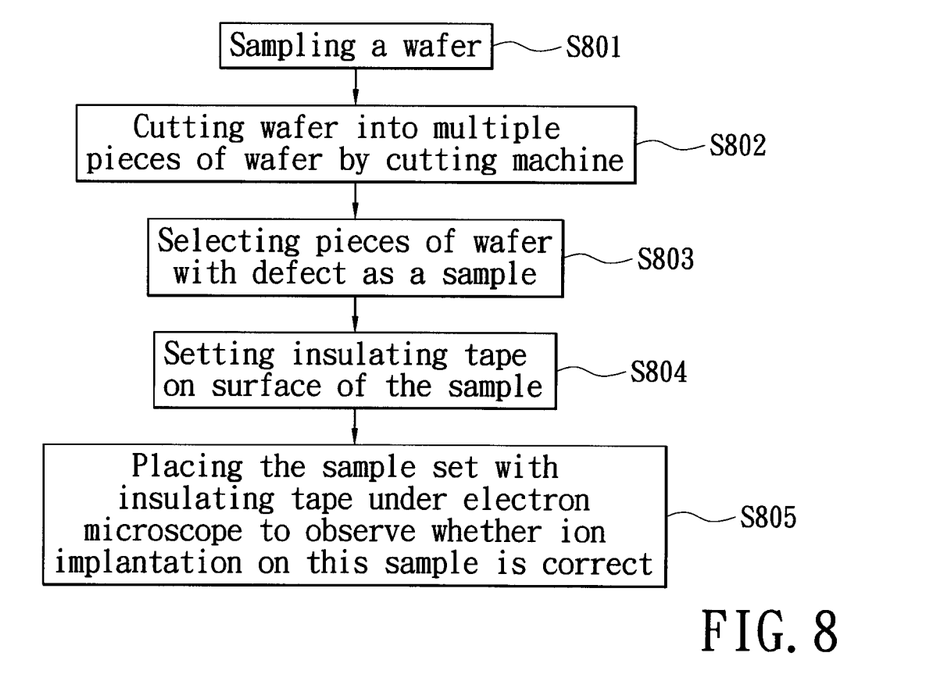
FIG. 8 is a flowchart of an eighth embodiment for the observation method of wafer ion implantation flaw/defect according to the present invention.
Figure 9:
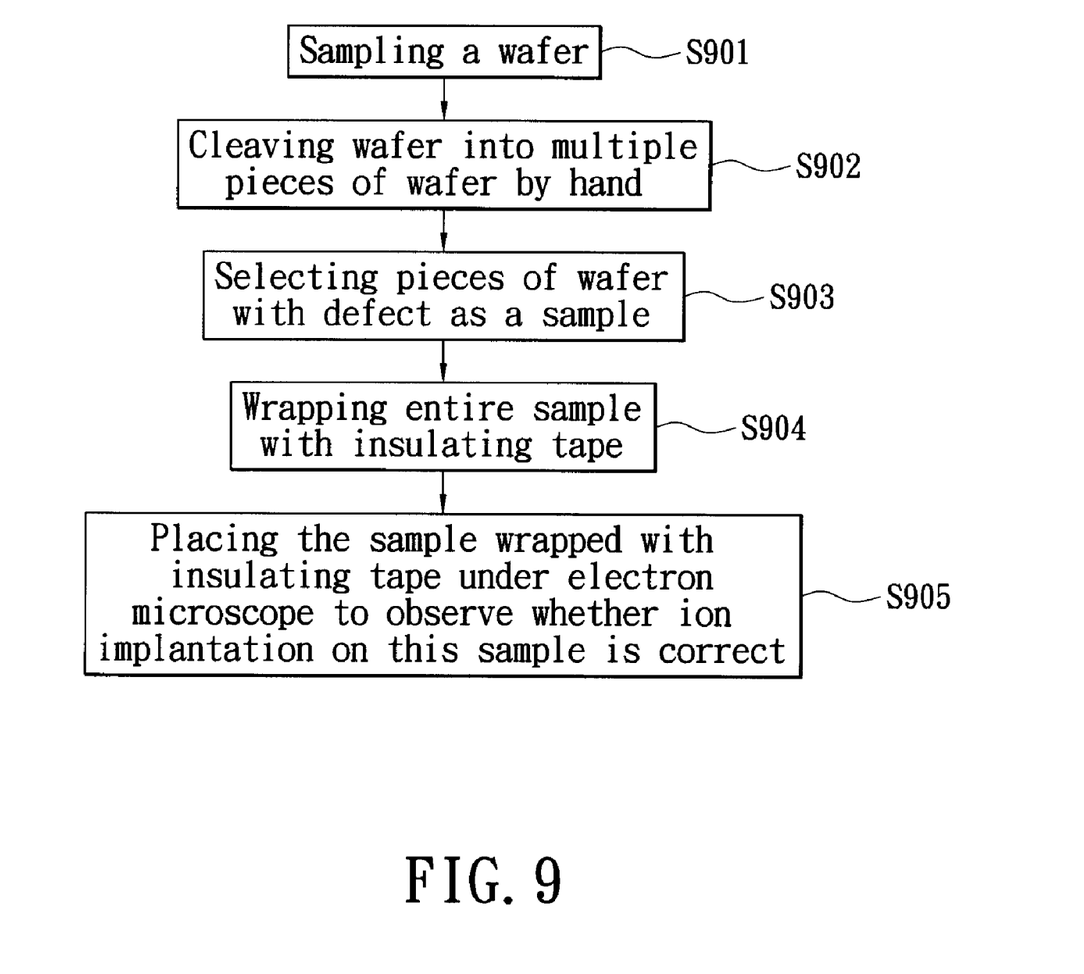
FIG. 9 is a flowchart of a ninth embodiment for the observation method of wafer ion implantation flaw/defect according to the present invention.

In the above-said step S602, wherein the wafer is divided into multiple pieces, other processes are also applicable, hereunder are a few embodiments listed for reference:

(a) as shown in FIG. 7 (seventh embodiment: S701~S705), cleaving the wafer into multiple pieces of wafer by hand (S702);

(b) as shown in FIG. 8 (eighth embodiment: S801~S805), cleaving the wafer into multiple pieces of wafer by using a cutting machine as a sample (S802);

In the aforementioned step S604, the way of placing the insulating tape on the sample has other alternative, as shown in FIG. 9 (ninth embodiment: S901~S905): wrapping the insulating tape on the sample (S904).

Figure 10:
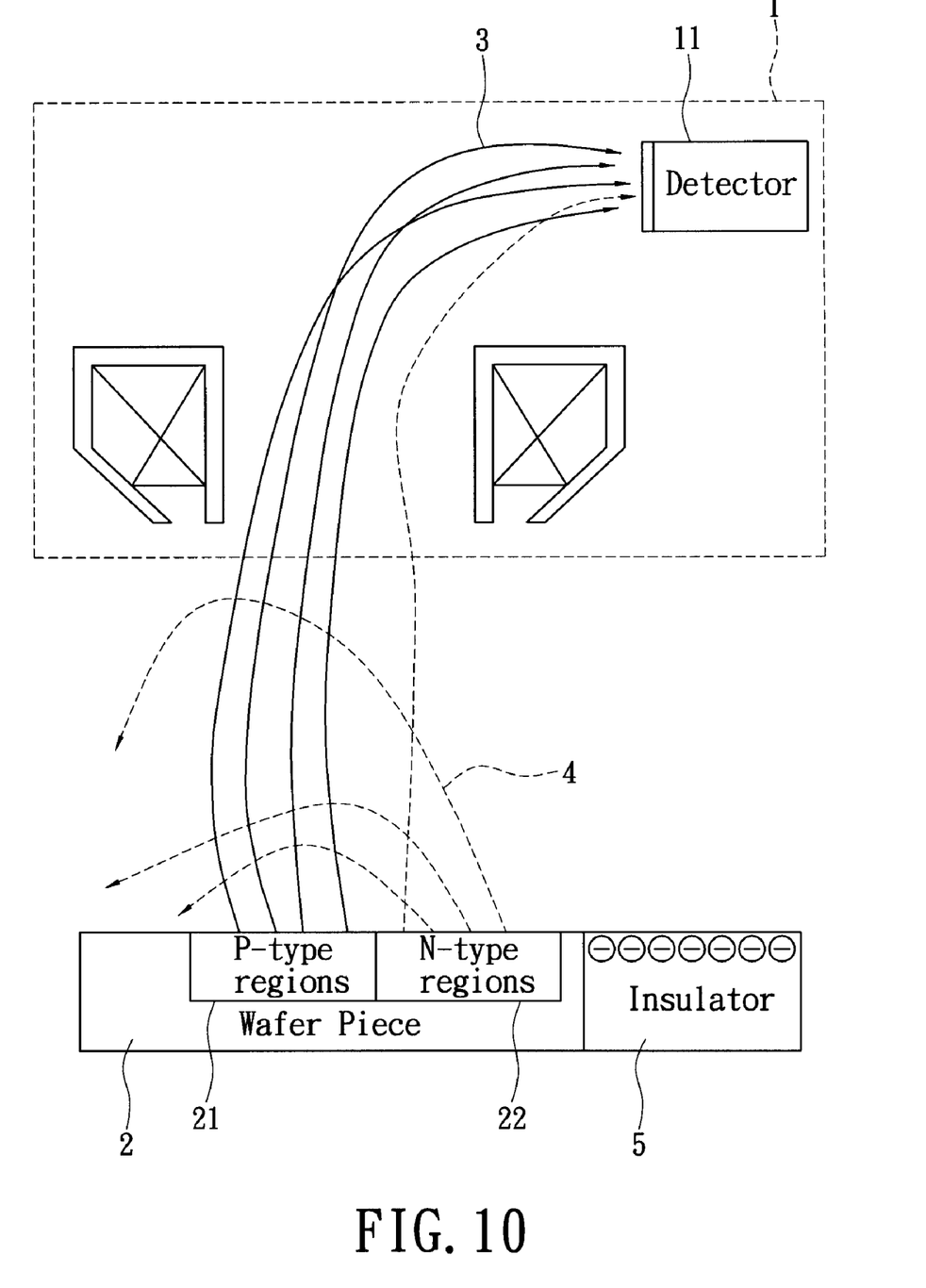
FIG. 10 is a diagram showing the possible modification of secondary electrons trajectories respectively from P-type regions and N-type regions when a negative insulator is nearby.

As shown in FIG. 10, the reason that present invention needs only to set an insulator on the surface of the sample to enable successful observation of ion implantation distribution on the sample 2 by the electron microscope 1 has its own theoretical foundation. After the electrons emitted from the electron microscope 1 bombard the sample 2, such an impact allows the P-type regions 21 and N-type regions 22 to emit secondary electrons 3, 4, and these secondary electrons 3, 4 move toward the detector 11 in the electron microscope 1, and as a result the detector 11 renders images upon reception of secondary electrons 3, 4. However, since the electrons emitted from the scanning electron microscope 1 and bombarding the insulator 5 mostly accumulate on the insulator 5, these accumulated electrons on the insulator 5 generate a strong electrical field effect, further affecting the motions of these secondary electrons 3, 4. Since the secondary electrons 4 emitted from the N-type regions 22 need more energy to reach the detector 11, they tend to be more easily influenced by the strong electrical field, resulting in greater deviation, thus the detector 11 receives more secondary electron 3 emitted from the P-type regions 21 than the secondary electrons 4 emitted from the N-type regions 22, which presents a clear contrast on the image rendered by the electron microscope. From the image of the sample 2 rendered under the electron microscope 1, it can be observed the brighter area indicates the P-type regions 21, and the darker area indicates the N-type regions 22. Compared with the normal wafer, if ion distribution is shown different from the one found in the normal wafer, it indicates the ion implantation in this sample 2 has failed.

Figure 11:
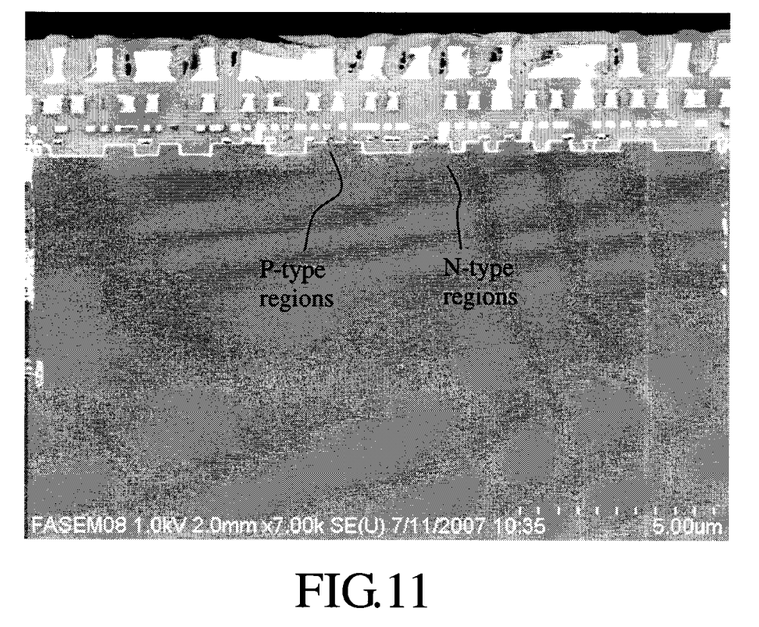
FIG. 11 Electronic image of a wafer without insulator on the surface thereof.

(1) As shown in FIG. 11, the solid lines indicate two areas presenting no clear boundary, impossible to tell the ion distribution therein.

Figure 12:
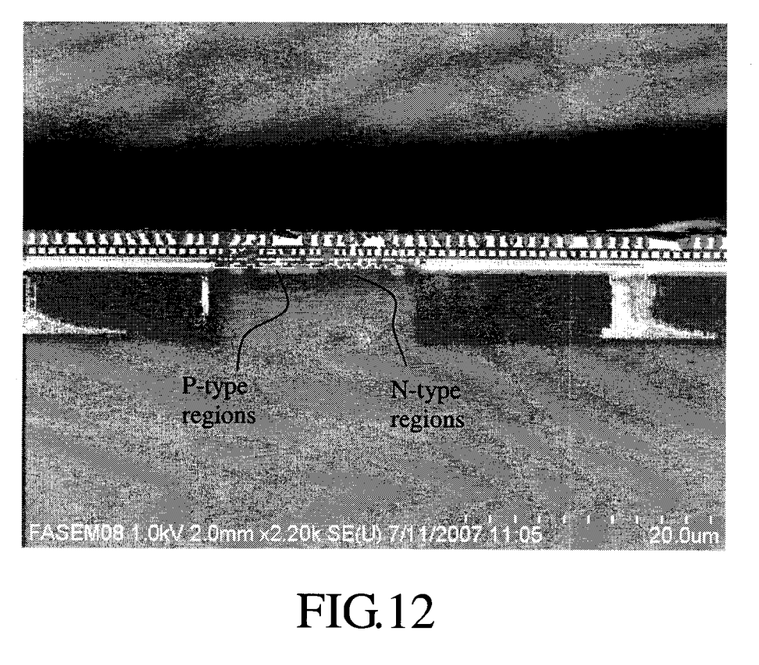
FIG. 12 Electronic image of a wafer with an insulating tape on the surface thereof.

(2) As shown in FIG. 12, the solid lines indicate two areas with clear differentiation, in which the brighter area indicates the P-type regions 21 and the darker area indicates the N-type regions 22.

Figure 13:
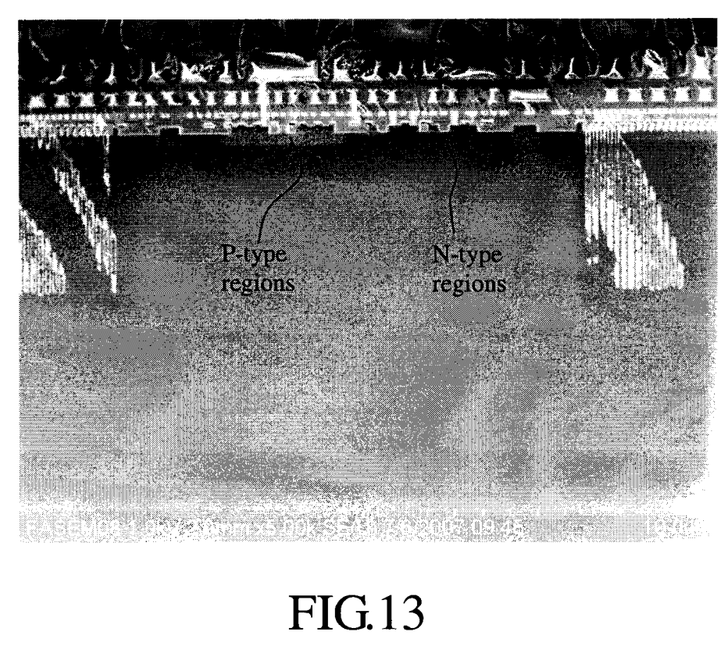
FIG. 13 Electronic image of a wafer with an epoxy placed on the surface thereof.

(3) As shown in FIG. 13, the solid lines indicate two areas with clear differentiation, more significant than the results shown in FIG. 12.

Figure 14:
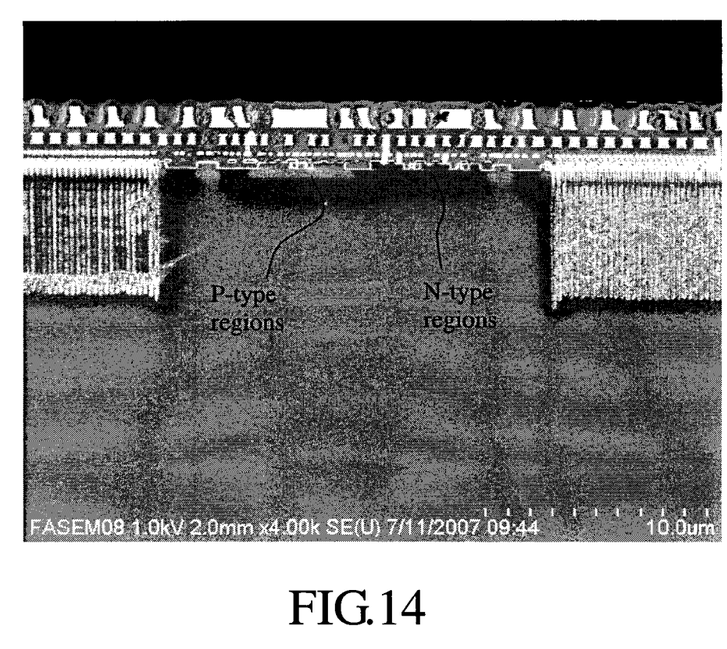
FIG. 14 Electronic image of a wafer wrapped with an insulating tape.

(4) As shown in FIG. 14, the solid lines indicate two areas with clear differentiation, more significant than the results shown in FIG. 12.

Figure 15:
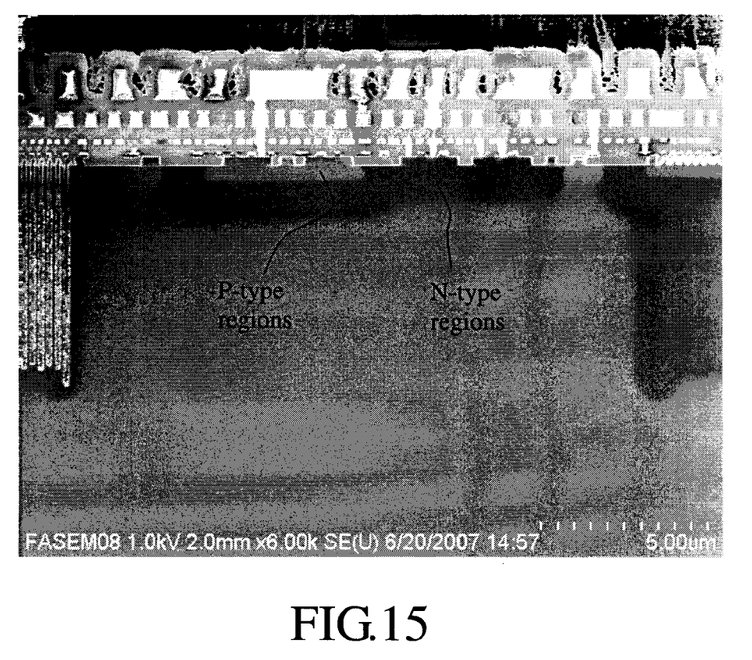
FIG. 15 Electronic image of a wafer placed with a photoresist on the surface thereof.

(5) As shown in FIG. 15, the solid lines indicate two areas with clear differentiation, more significant than the results shown in FIGS. 12 to 14.

Figure 16:
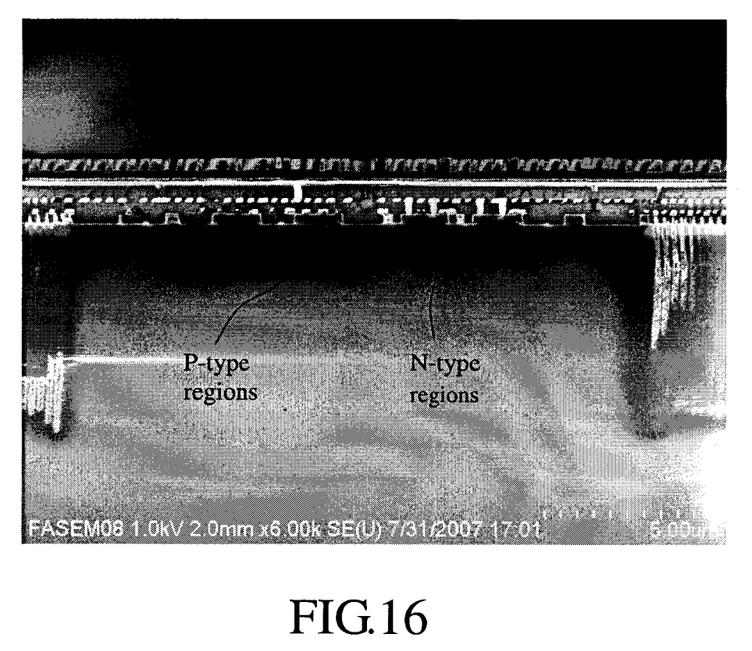
FIG. 16 Electronic image of a wafer placed with another photoresist on the surface thereof.

(6) As shown in FIG. 16, the solid lines indicate two areas presenting no clear contrast, impossible to tell the ion distribution therein.

By using the observation method of ion implantation defect according to the present invention, since the placement of insulator 5 on the surface of the sample 2 is relatively easier, as compared with immersion in chemical decoration which requires in-situ experiences of engineers for each successful operation, the possibility of successful operation can be improved, thereby accordingly offering nearly 100% of repeatability for analysis results. On the other hand, since the preparation of wafer samples does not require processes of polishing and chemical decoration, time spent on entire analysis workflow can be thus significantly reduced.

The aforementioned descriptions simply illustrate the preferred embodiments according to the present invention, not being intended to limit the scope of the present invention. All changes and modifications equivalent in effect based on the present specification are deemed to be encompassed by the scope of the present invention defined by the subsequent claims.

What is claimed is:

1. An observation method of wafer ion implantation defect, comprising the following steps:
   cleaving a wafer into multiple pieces of wafers;
   selecting a piece of wafer with defect as a sample, and setting an insulator on the surface thereof;
   using a scanning electron microscope to observe whether the ion implantation of the sample is successful.

2. The observation method of wafer ion implantation defect according to claim 1, wherein the insulator is an insulating tape, and the insulating tape is set on the surface of the sample.

3. The observation method of wafer ion implantation defect according to claim 1, wherein the insulator is an insulating tape, and the insulating tape wraps the sample.

4. The observation method of wafer ion implantation defect according to claim 1, wherein the insulator is a photoresist, and the photoresist is dispersed on the surface of the piece of wafer with defect.

5. The observation method of wafer ion implantation defect according to claim 1, wherein the insulator is epoxy resin.

6. The observation method of wafer ion implantation defect according to claim 5, wherein the epoxy resin is set on the surface of the sample.

7. The observation method of wafer ion implantation defect according to claim 1, wherein the acceleration voltage range of the electron microscope is set to be within 1000 volts~3000 volts.

8. The observation method of wafer ion implantation defect according to claim 1, wherein the working distance range of the electron microscope is set to be between 1.5 mm~8 mm.

9. An observation method of wafer ion implantation defect, comprising the following steps:
   sampling a wafer;
   cleaving the wafer and forming multiple pieces of wafers;
   selecting a piece of wafer with defect as a sample;
   setting an insulating tape on the sample; and
   placing the sample installed with the insulating tape under a scanning electron microscope to observe the state of the ion implantation on the wafer with defect.

10. The observation method of wafer ion implantation defect according to claim 9, wherein the wafer is cloven into multiple pieces of wafer by hand.

11. The observation method of wafer ion implantation defect according to claim 9 wherein the wafer is broken into multiple pieces of wafer by hand.

12. The observation method of wafer ion implantation defect according to claim 9,
   wherein the wafer is cloven into multiple pieces of wafer by using a cutting machine.

13. The observation method of wafer ion implantation defect according to claim 9,
   wherein the insulating tape is set on the upper surface of the piece of wafer with defect.

14. The observation method of wafer ion implantation defect according to claim 9, wherein the insulating tape wraps the piece of wafer with defect.

* * * * *